(12) United States Patent
Sevy (10) Patent No.: US 7,878,418 B2
(45) Date of Patent: Feb. 1, 2011

(54) INTEGRATED, ESSENTIAL-OIL ATOMIZER

(76) Inventor: Early Vaughn Sevy, 4560 N. Tomahawk Dr., Enoch, UT (US) 84720

(*) Notice: Subject to any disclaimer, the term of this patent is extended or adjusted under 35 U.S.C. 154(b) by 197 days.

(21) Appl. No.: 12/247,755

(22) Filed: Oct. 8, 2008

(65) Prior Publication Data

US 2010/0084484 A1 Apr. 8, 2010

(51) Int. Cl.
*A62C 5/02* (2006.01)
(52) U.S. Cl. .............. 239/8; 239/69; 239/338; 239/340; 239/346; 239/351; 239/370; 239/590.3; 239/124; 128/200.18; 128/200.21; 261/DIG. 88
(58) Field of Classification Search .............. 239/8, 239/11, 67, 69, 338, 340, 342, 346, 351, 239/369, 370, 124; 128/200.14, 200.18, 128/200.21; 261/78.2, DIG. 88; 422/123
See application file for complete search history.

(56) References Cited

U.S. PATENT DOCUMENTS

| | | | | |
|---|---|---|---|---|
| 2,826,454 | A | * | 3/1958 | Coanda ............... 239/338 |
| 5,248,448 | A | * | 9/1993 | Waldron et al. ........... 261/78.2 |
| 5,549,247 | A | * | 8/1996 | Rossman et al. ........... 239/338 |
| D491,258 | S | | 6/2004 | Sevy |
| D492,020 | S | | 6/2004 | Sevy |
| D509,893 | S | | 9/2005 | Sevy |
| D520,129 | S | | 5/2006 | Sevy |
| D526,710 | S | | 8/2006 | Sevy |
| 7,407,118 | B2 | | 8/2008 | Sevy |
| 7,712,683 | B2 | * | 5/2010 | Robert et al. ........... 239/346 |

OTHER PUBLICATIONS

Aroma-Globe™ Essential Oil Diffuser/Nebulizer Diffuser World,Aug. 10, 2008, p. 1 http://www.diffuserworld.com/aromaglobATM-essential-oil-diffusernebulizer-p-10.html.
Nebulizing Diffuser, Betterherbs, Oct. 8, 2008, http://betterherbs.serrahost.com/Detail.bok?no=397.
Auroma Nebulizer for the House, Shop.com, Oct. 8, 2008, p. 1 http://www.shop.com/Auroma_Nebulizer_for_the_House_diffuser-46805905-p!shtml.
Aura Cacia Electric Diffuser House Model, Shop.com, Oct. 8, 2008, p. 1, http://www.shop.com/Aura_Cacia_Electric_Diffuser_House_Model_diffuser-46805768-p!.shtml.
Essential Air Room Diffusers, Leyden House, Oct. 8, 2008, p. 1 http://www.leydenhouse.com/diffusers.html.

* cited by examiner

*Primary Examiner*—Steven J Ganey
(74) *Attorney, Agent, or Firm*—Pate Pierce & Baird (57) ABSTRACT

An atomizer provides a control of duty cycle or a motor driving a diaphragm pump. By providing precise, high-speed flow through an eductor nozzle, improved atomization occurs. However, to control the total volume of atomized liquid discharged, the delay time between operational time periods may also be controlled. Thus, a very effective atomizer provides economical use of essential oils by control duty cycle. Precision modeling provides highly integrated subsystems providing superior performance and reliability.

18 Claims, 9 Drawing Sheets

INTEGRATED, ESSENTIAL-OIL ATOMIZER

BACKGROUND

1. The Field of the Invention

This invention relates to atomizers and, more particularly, to novel systems and methods for integrating air supplies, reservoirs and atomizers into an integrated system.

2. The Background Art

Various mechanisms for treating an environment with moisture, medicaments, and the like have been developed using boilers, heaters, fans, and so forth. Aroma therapy involves evaporation, distribution, or other entrainment of volatiles, essential oils, or the like into breathing air, an atmosphere of a room, or other enclosed space. Applicant has previously developed various mechanisms for distributing atomized liquids into the atmosphere. Likewise, various systems for heating or dissolving aromatic or oil-based materials in a solvent to promote evaporation into the atmosphere have also been relied upon in the art. Meanwhile, various medical devices provide humidification of a space such as a "steam tent" or the like.

Spray painting has long used various types of spray devices to apply paint onto surfaces. However, with such systems, pumps are typically very heavy on the order of several pounds or tens of pounds. Also, sprayer systems are typically not integrated because the supply of paint is a large container weighing from about 8 to about 40 pounds. Accordingly, a painter desires to have a very small spray head on a handle. Thus, it has been more useful to separate a reservoir from a sprayer and from a pump.

However, in aroma therapy, it would be an advance in the art to accommodate space, aesthetics, weight, stability, simplicity of use, ease of use, storage, and the like. Moreover, in handling materials such as essential oils, one should take care not to damage finishes, stain clothing or fabrics, and so forth. Accordingly, it would be an advance in the art to provide an integrated system having suitable weight for stability, a sufficiently small size so excessive footprint and volume are not occupied on a dresser, table, or a night stand. It would be an advance to provide a system easily, safely, and securely located anywhere within a room. Likewise, it would be an advance in the art to provide an aesthetically pleasing shape integrating all of the functions required for evaporating or atomizing a scent, perfume, essential oil, or other material desired to be distributed within an ambient environment.

It would also be an advance in the art to provide an apparatus having long life, inexpensive components, easily replaceable parts, few moving parts, few wearing parts, and simple assembly and operation. It would also be an advance in the art to provide an aroma therapy generator or atomizer that could feed from standard commercial bottles, conventionally used to contain essential oils, by direct connection to the atomizer. This could further eliminate any need to pour and otherwise chance spilling drops of damaging oil or other liquids on furniture or fabrics.

It would also be an advance in the art to provide control over such a mechanism in order to optimize the use of materials. For example, it would be an advance in the art to provide some control over the amount of an expensive oil atomizing into the atmosphere.

However, balancing the need to atomize an oil into a very fine dispersion in air acts opposite or requires an opposite design criterion compared to minimizing the amount of material used. Thus, it would be an advance in the art to provide an atomizer that provides a better atomization or a smaller mean or average size of droplet in the distribution of atomized droplets compared with prior art devices capable of atomizing.

BRIEF SUMMARY OF THE INVENTION

In view of the foregoing, in accordance with the invention as embodied and broadly described herein, a method and apparatus are disclosed in one embodiment of the present invention as including a system having a housing for a pump driven by an oscillating motor to draw liquids from a reservoir and distribute them through an eductor into the atmosphere.

In one embodiment, a separator after the eductor relies on direction change and momentum of impact to further comminute the droplets into a more finely atomized mist, while separating out comparatively larger droplets in a comparatively very short distance. Thus, large chambers dedicated to permitting larger droplets to fall out of a stream or flow of air may be avoided for a more compact device.

In one embodiment, a method of aroma therapy may include providing an atomizer, including an eductor and a separator. The atomizer may be connected directly to a reservoir such as a bottle from a supplier of a fragrance, essential oil, or the like. The atomizer may be connected directly to a pump anchoring the atomizer to a supporting surface by weight, stability, base, or the like.

The method may include adjusting an electronic controller to control at least one of a duration of operation and a duration of a delay between periods of operation of the pump. Operating the pump pressurizes ambient air into a flow through the atomizer. The flow of air through a nozzle educts surrounding air, which creates a vacuum or reduced pressure, drawing a liquid directly from the reservoir into the flow of air.

The method may involve atomizing the liquid into droplets by virtue of the educting stream of air as well as by the entrained droplets colliding against a wall of the separator. The separator, flowing the air stream at reduced velocity, separates the droplets by size, the smaller droplets moving with the air, and the larger ones drifting out or agglomerating at walls and other obstructions. Comparatively larger droplets are recovered and directed back into the reservoir.

Comparatively smaller droplets are passed from the atomizer out through the separator chamber and associated obstructions with the flow of air. The method simultaneously limits net outflow of the liquid and decreases mean droplet size. A user controls these by selectively setting the duty cycle of the pump, the fractional time of operation compared to total elapsed time. In some embodiments, the duty cycle may be controlled by controlling the ratio of the duration of operation to the duration of a delay plus the duration of operation.

A first connector of the atomizer may connect directly to the pump, a second connector thereof directly to the reservoir, and a third connector thereof directly to a distributor. In fact, the atomizer may be homogeneously molded with the first, second, and third connectors as a unit. A suitable polymeric or even elastomeric resin may be used to mold the atomizer.

In some embodiments, a method may provide a housing, a motor being disposed inside the housing and electrically powered to drive a pump. The housing may further include a lock securing the atomizer to the pump. The pump may be located in the housing having a filter disposed in an aperture thereof. The recess or aperture receiving a power cord providing power to the motor may serve this function. The aperture may also hold a grommet serving to support stress on the cord. Meanwhile, a gap may be provided therearound to pass the flow from the environment to the pump by way of the housing.

In some embodiments, the pump comprises a pump body fitted with a valve body as a plate captured in a pinch slot to support pressure between the pump body and valve body plate. Seals positioned about openings passing the flow into and out of the pump may minimize pressure exposure of the structures of the pump. This is an improvement over conventional gaskets by being sized to fit within from about one to about three diameters, typically about two diameters, of the aperture corresponding to each such face seal.

A method may provide a separator plate controlling outflow from a separator chamber, separating comparatively larger droplets from comparatively smaller droplets prior to exit of the comparatively smaller droplets from the atomizer, entrained in the air flow. An eductor may include a nozzle having a minimum effective diameter discharging the flow therethrough and into an aperture spaced therefrom a distance of from about one to about 10 times the minimum effective diameter of the aperture of the nozzle.

The method may include a pump disposed within a housing, driven by a motor, and comprising a diaphragm compressing air and providing a flow thereof at a pressure greater than ambient pressure. The motor may have a coil and magnet operably connected to reciprocate an armature magnet back and forth to move the diaphragm.

A control system may provide infinitely variable adjustment between extremes (maximum and minimum values), to be set by a user arbitrarily selecting a duration of operation, duration of deactivation between periods of operation of the motor, or both.

In some embodiments, a bottle containing a liquid comprising a scent, such as an essential oil may be selected from a vendor and used directly by connection to the atomizer, such as by threading the atomizer directly to the bottle. The atomizer may be connected directly to the pump. The atomizer may be fixed to the pump or the housing by a fastening mechanism such as a rotating bayonet connection or the like. Anchoring the atomizer by the bulk, weight or both of the pump and housing assembly reduces the chance of breakage or spilling of an atomizer system sitting on a supporting surface.

In operation, the eductor nozzle draws directly from the bottle a portion of the liquid by momentum transfer associated with eduction. That is, eduction is the transfer of momentum from a high speed stream to another stream or quiescent body of fluid. The momentum of the comparatively high speed stream of the nozzle, fed by the pump, tends to both accelerate and atomize the educted (drawn) portion of liquid into droplets.

Spraying the droplets into a separator removes droplets insufficiently small to be carried indefinitely by ambient air movement. The separator and flow are sized to release with the air flow those droplets having an effective diameter of from about 1 micron to about 5 microns. Smaller droplets tend to evaporate into the air stream, while larger ones tend to settle down or agglomerate on surfaces to be returned to the reservoir.

In some embodiments, the pump connects directly to the atomizer, the pump providing the air flow, powering the increase first in pressure, and then in the velocity of the flow by constricting the flow through a nozzle. The high speed flow of air educts surrounding air, drawing down pressure in a chamber therearound, which chamber and reduced pressure draw the liquid from the bottle into the flow as droplets.

The atomizer may typically have a first fitting, second fitting, and third fitting all homogeneously molded with it, so the first fits directly and receives securely the bottle, the second fitting contains the eductor, and a third contains a distributor releasing the flow into the ambient.

In some embodiments, conducting aroma therapy may involve selecting the liquid to be an essential oil containing substantially no diluents, selecting by a user a first time period corresponding to operation of the pump, arbitrarily selected between a first minimum time and a first maximum time, and selecting by a user a second time period corresponding to a delay in operation of the pump. The delay may be arbitrarily selected between a second minimum time and a second maximum time.

Typically, an apparatus may be constructed to contain a housing, a pump disposed within the housing (typically of a type having a diaphragm compressing air drawn from the ambient), and a magnetic, electric motor driving the pump. The motor may be an oscillating type, having a coil and a magnet (electromagnet) connected to reciprocate an electric field. The electromagnet drives a permanent magnet back and forth to oscillate the diaphragm. The pump may have two diaphragms in symmetric arrangement to reduce vibration.

A control system operably connected to the coil may control electricity flowing to the coil, including voltage, current, off and on conditions, and so forth. The control system may include an actuator adjustable by a user to selectively and arbitrarily control the duration of delivery of electrical energy to the coil. A user may selectively and arbitrarily control a delay between adjacent periods of continuous delivery of electrical energy to the coil. A user may also arbitrarily control the duration of delivery of electrical energy to the coil and a delay between adjacent periods of continuous delivery of electrical energy to the coil.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 1 is an exploded view of one embodiment of an integrated apparatus in accordance with the invention;

FIG. 2 is a more detailed exploded view of one embodiment of a rear half of the housing of FIG. 1 showing components installed within and without the housing shell;

FIG. 3 is a perspective view of the apparatus of FIGS. 1-2 in an assembled configuration;

FIG. 4 is a rear quarter perspective view of the apparatus of FIGS. 1-3 illustrating the control panel;

FIG. 5 is an exploded view of the pump mechanism and the armature portions of the motor attached to swing arms to drive the diaphragms of the pump;

FIG. 6 is an exploded, rear quarter view of the front half of the housing of the apparatus with its contents, including the motor and pump;

FIG. 7 is a partially-exploded perspective view of the atomizer portion of the apparatus illustrating its connection mechanisms to connect to the pump and housing;

FIG. 8 is a cross-sectional, side-elevation view of one embodiment of the apparatus of FIGS. 1-7; and FIG. 9 is a detailed cross-sectional, side elevation view of the pump body and the atomizer body in accordance with the invention.

DETAILED DESCRIPTION OF THE PREFERRED EMBODIMENTS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figure 1:
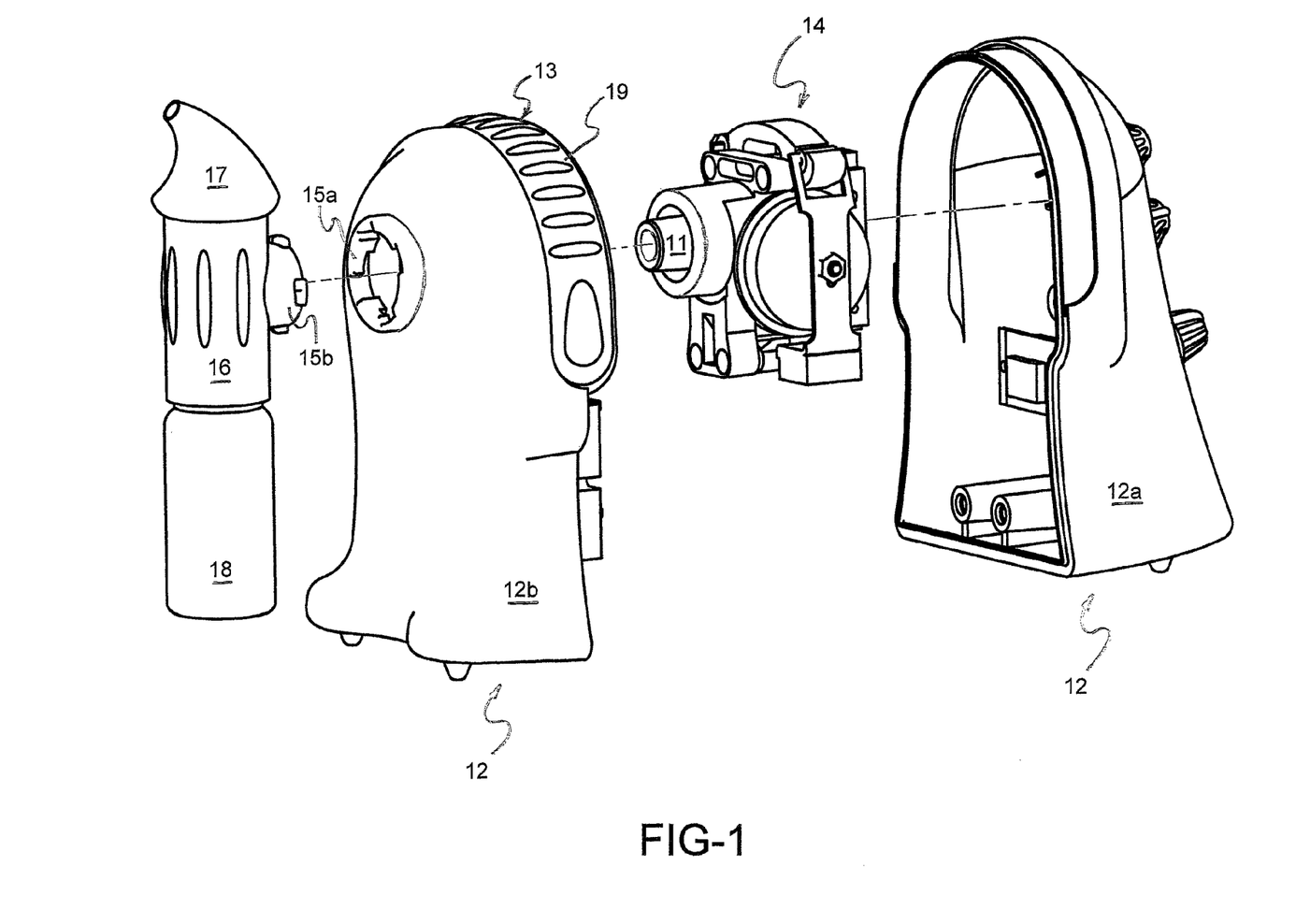

Referring to FIG. 1, an apparatus 10 in accordance with the invention may include a rear portion 12a and a front portion 12b. The housing 12 may be provided with some amount of trim 13 providing more aesthetic appeal as well as servicing the need for a secured gripping region 13. Within the housing 12, may be located a pump 14. In the instant embodiment, the pump 14 may be of a diaphragm type, and may be of a double-diaphragm type. An outlet 11 from the pump may protrude into or through a housing connector 15b mated to secure to a connector 15b as part of an atomizer 16. In the illustrated embodiment, the atomizer 16 may secure such as by threads or the like to a reservoir 18. Air from the pump 14 drives atomization in the atomizer 16 to discharge atomized liquids out the director 17. The liquids are drawn by the atomizer 16 from the reservoir 18. The atomizer 16, as well as the trim 13 may be provided with grips 19 to assist a user in manipulating these portions of the apparatus 10.

Figure 2:
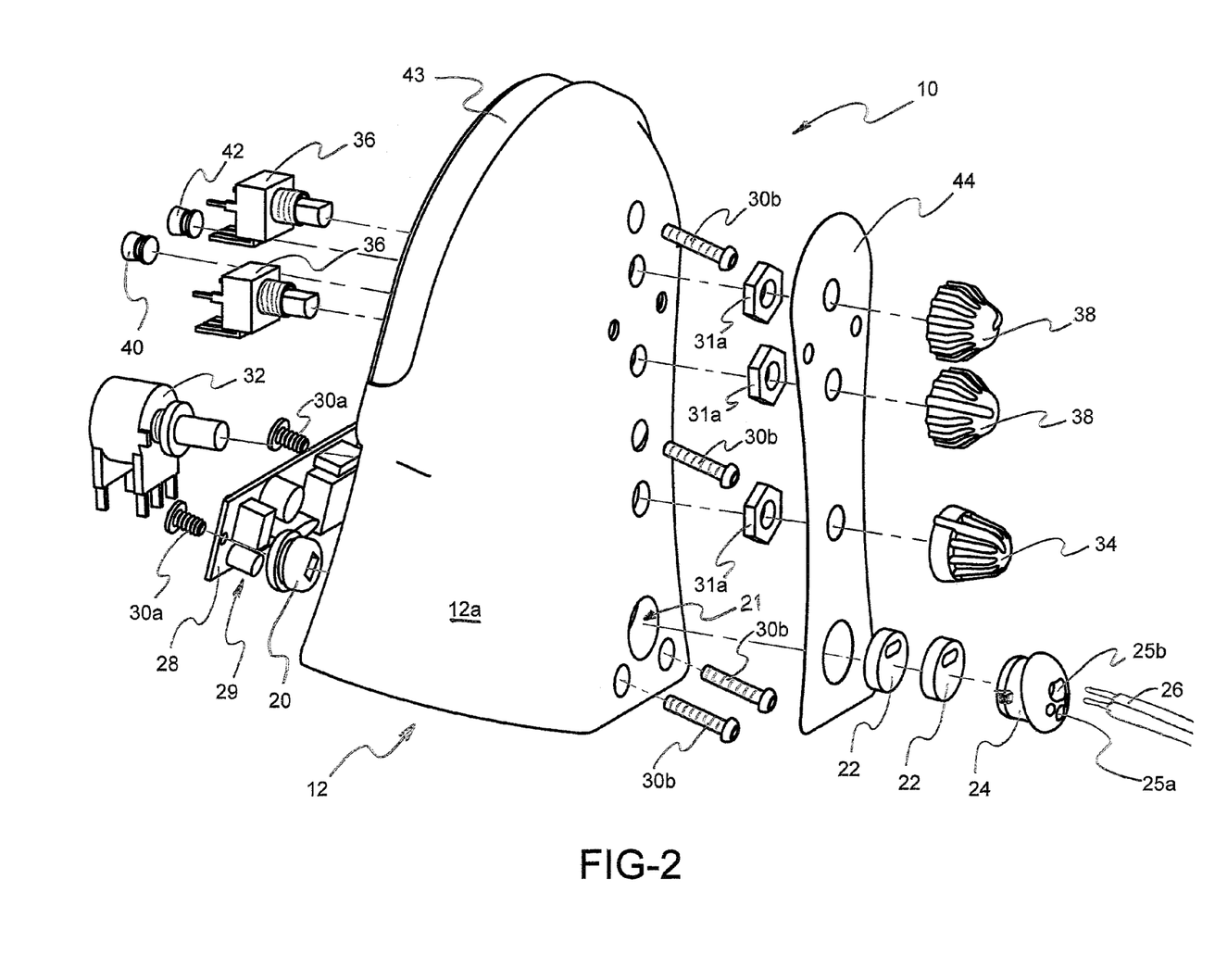

Referring to FIG. 2, the apparatus 10, in one embodiment, may include a portion 12a of the housing 12 provided with a grommet 20 to capture and maintain a cord 26 in a recess 21. Typically, a grommet 20 may contain structures such as detents, circuitous paths, blocks, clamps, or the like effective to restrain a cord 26 and to take strain from the conductors of such a cord 26. Thus, the grommet 20 may also be referred to as stress relief 20.

The recess 21 may also contain filter elements 22 or filters 22. In the illustrated embodiment, a cap 24 maintains the filters 22 within the recess 21. Apertures 25a provide for passage of air into the housing 12. Likewise, an aperture 25b provides space for a cord 26 to pass through the cap 24, the filters 22, and the recess 21 to be captured by the grommet 20 or stress relief 20.

A printed circuit board 28 may include various control circuitry 29 or components 29 interconnected by the printed circuit board 28. The control circuitry 29 or componetry 29 may include various devices interconnected to provide implementation of controls for the apparatus 10.

Various fasteners 30, 31 may be implemented to secure the various components of the apparatus 10. For example, the fasteners 38 may secure the circuit board 28 to the housing 12. Similarly, the fasteners 30b may secure the front portion 12b of the housing 12 to the rear portion 12a.

Other fasteners 31a, shown as nuts in the illustrated embodiment may secure controllers 32 such as a rheostat 32, for example, to the housing 12 through a penetration configured to receive the controller 32 and present a portion thereof for connection to a control knob 34. Likewise, other controllers 36, such as, for example, potentiometers 36 may pass through apertures in the housing 12 to be secured by fasteners 31a. Likewise, a portion of the control devices 36 may pass through the aperture and the fastener 31a in order to receive control knobs 38 secured thereto to operate the controls 36.

Indicators 40, 42 may likewise penetrate through apertures in the housing 12 to be visible to a user. For example, in one embodiment, the indicator 40 may be a light emitting diode (LED) of a green color to indicate that the pump 14 is in operation. In contrast, the indicator 42 may be another LED having a color such as amber indicating that the pump 14 is on standby. Thus, an indicator 42 may indicate that power is supplied to the apparatus, but the control mechanisms are not permitting operation of the pump 14 at that time.

The housing 12 may be provided with a recess 43 in each portion 12a, 12b to receive the trim 13. Likewise, a legend 44 may be implemented by an overlay 44 containing instructions, demarcations, identifications, and so forth corresponding to the control knobs 34, 38. Apertures in the overlay 44 may provide for visibility of the indicators 40, 42, passage of control shafts of the controllers 32, 36 for engagement with the control knobs 34, 38, and so forth.

Figure 3:
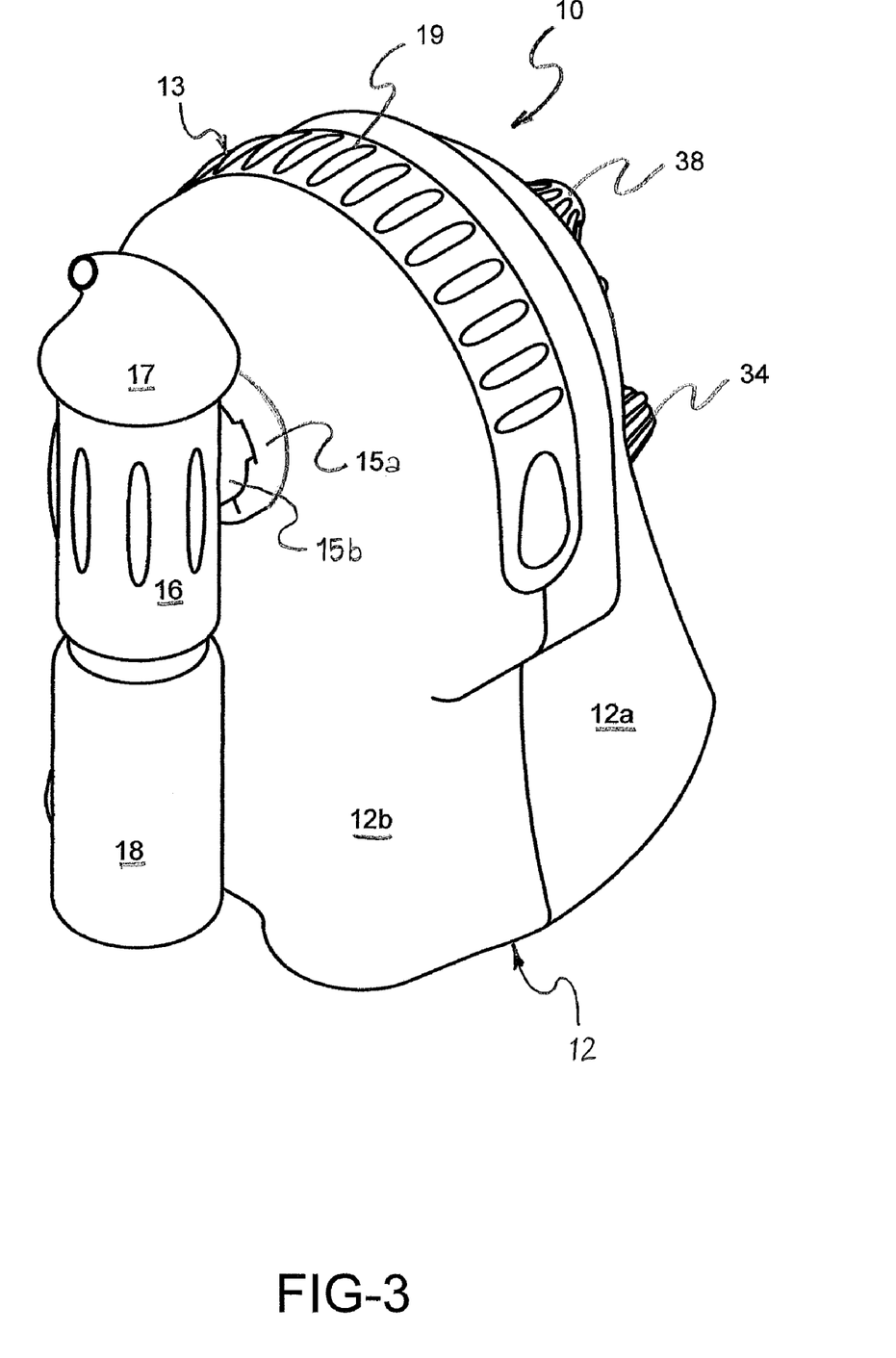
Figure 4:
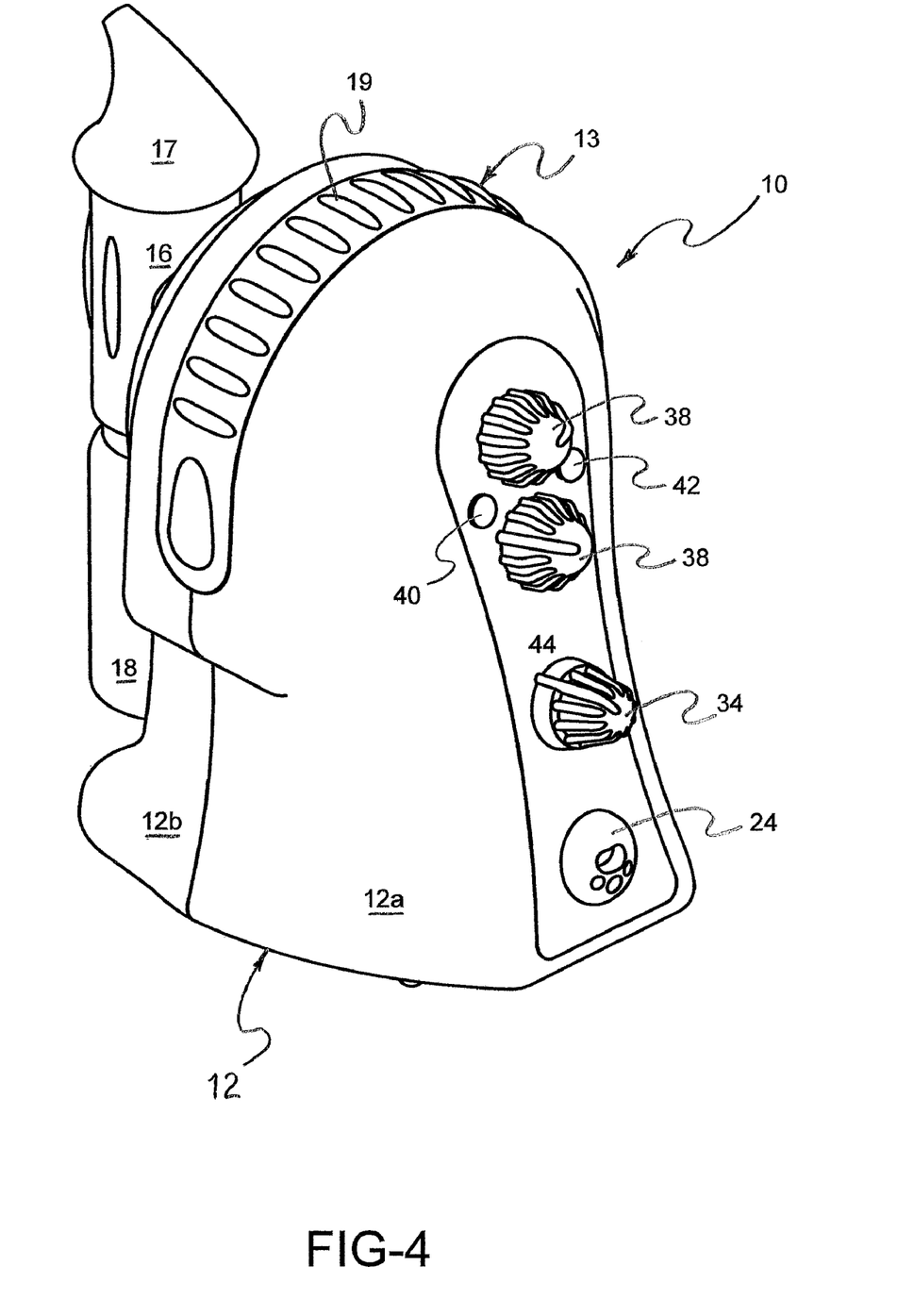

Referring to FIGS. 3-4, the apparatus 10, once assembled, may present an enclosure 12 comprising the two portions 12a, 12b. The connector 15 may secure and register the atomizer 16 to the housing 12. Likewise, the control knobs 34, 38 may protrude from the rear of the housing 12 to present the access desirable by a user. Likewise, the overlay 44 applied to the surface of the housing 12 may provide demarcations, graduations, and other markings and instructions to provide context for the use of the control knobs 34, 38 as well as the reading or interpreting of the indicators 40, 42.

In the illustrated embodiment, the atomizer 16 is connected to a reservoir 18 secured thereto, and a distributor 17 enclosing the atomizer 16 or the top thereof. The entire assembly may be removed from the pump 14 and housing 12 by release a suitable connectors 15a, 15b. In one embodiment, a connector 15 may include tabs and slots such as a bayonet connector in order to provide for insertion of the connector portion 15b into the connector portion 15a, with securement to follow by relative rotation therebetween.

Comparative dimensions and comparative weights of the atomizer 16, together with the reservoir 18 and distributor 17 may typically be comparatively less than those of the housing 12 and its contents. Including the controls 32, 36, pump 14, and other equipment required to support the atomizer 16, the net weight contained by the housing 12 may be substantially more than that of the atomizer 16 and its connected reservoir 18 and distributor 17. Moreover, the dimensions of the base of the housing 12 may also provide leverage against tipping, tending to move the center of gravity of the apparatus 10 considerably away from the atomizer 16. Thus, the housing 12 and its contents provide a stable platform to support the atomizer 16 on a surface.

Figure 5:
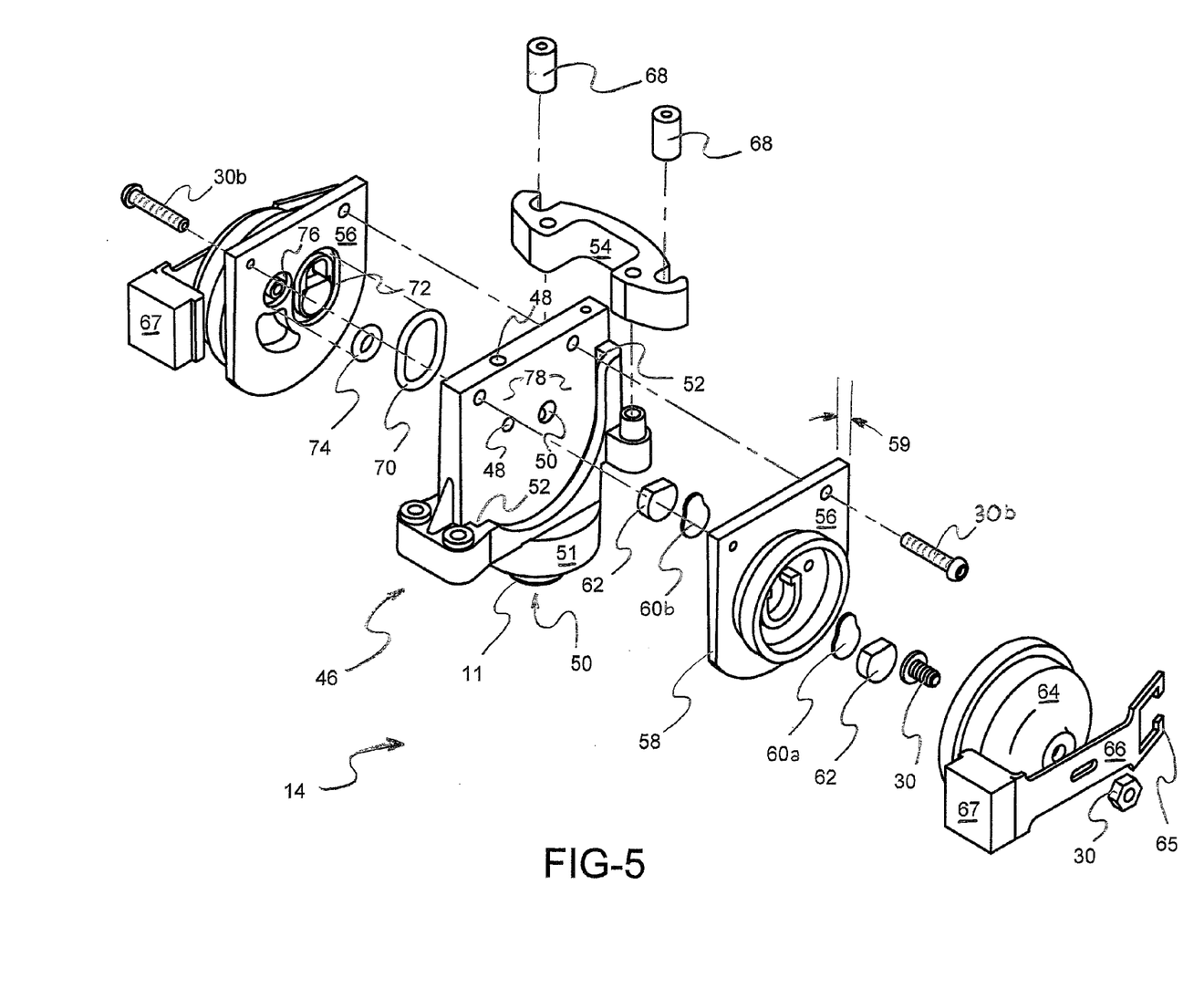

Referring to FIG. 5, the pump 14 may include a pump body 46 or body 46 central thereto. The body 46 may have formed therein a passage 48, here illustrated as it encounters two faces of the body 46. The passage 48 provides an inlet for air coming from within the housing 12 into the pump. Likewise, a passage 50 originates from a face of the body 46, and eventually exits through the outlet 11 of the pump 14.

Meanwhile, a flange 51 or nose 51 may be fitted to contact the housing 12, and particularly the back portion 12b of the housing 12. The flange 51 or nose 51 provides registration of the pump 14, with corresponding registration of the outlet 11 where the outlet 11, may engage the atomizer 16.

In the illustrated embodiment, a slot 52 or pinch slot 52 receives a valve body 56 therein, thus providing support along a large portion of the periphery of the valve body 56. Thus, the passages 48, 50 are operably connected to compression chambers 53 in the respective valve bodies 56. A retainer 54 may secure the valve bodies 56 to opposite faces of the pump body 46. The tapered face 58 of each valve body 56 illustrates that each is formed with an angle 59. Thus, the pinch slot 52 may more easily capture but then tightly secure the valve body 56 once it is fully inserted into the pinch slot 52.

Covering and associated with the apertures in the pump body 56 corresponding to the passages 48, 50 in the pump body are reeds 60 or flappers 60 secured by keepers 62. The reeds 60 act as one-way valves, each permitting flow in one direction and resisting flow in the opposite direction. Accordingly, each of the compression chambers 53 may draw air in through the passage 48, then seal off the passage 48 with the reed 60. The passage 50 may accordingly be sealed off against back flow, but opened to be accessible by movement of the reed 60b opposite the reed 60a. Actually, the reeds 60a, 60b are not exactly opposite one another but rather, each is on an opposite side of the valve body 56, and services an aperture for one of the passages 48, 50.

The reeds 60a, 60b provide substantially instantaneous valving in accordance with the pressure within and without the chamber 53. Thus, air is drawn into the chamber 53 by the diaphragm 64 as it moves away from the valve body 56. Similarly, air is pushed back from the diaphragm through the valve body 53 and into the passage 50 by the diaphragm 64 under the control of the reed 60b.

Typically, a diaphragm 64 may be formed in a single piece to secure about the chamber 53. Thus, a diaphragm 64 may form a sealing and a closure for the chamber 53. Each diaphragm 64, of which there may be a single diaphragm 64, or multiple diaphragms, may be secured to the pump 14 by fasteners 30 to a swing arm 66. The swing arm 66 itself may include a yoke 65 secured to a hinge 68. Meanwhile, opposite the yoke 65 a magnet 67 secured to the swing arm 66 operates as an armature 67 in conjunction with the drive mechanism (i.e., electromagnet).

The yoke 65, capturing a hinge 68, such as a resilient tubing may provide a comparatively wear-free, damping, long-lived attachment mechanism. The hinges 68 recessed into the retainer 54 each provide a pivot axis for the respective swing arms 66 about the yokes 65 thereof.

Various seals 70 may be provided to both limit and secure passage of air through the pump 14. For example, a seal 70 may be formed as an 'O' ring fitted into a slot 72 or groove 72. Accordingly, the seal 70 provides securement of the flow of air from the passage 50 into the valve body 56. Likewise a seal 74 may be configured to fit in a groove 76 or slot 76 sealing against leakage of air between the passage 48 and the valve body 56. Thus, the seals 70, 74 fit between the valve bodies at the grooves 72, 76, and against the faces 78 of the pump body 46 to effect their sealing.

The diaphragms 64 operate by the oscillation of the armatures 67 driving the swing arms 66 to pivot about their yokes 65 and hinges 68. Accordingly, the armatures 67 pivot yet travel in an almost linear fashion, driven by electromagnetic forces.

Figure 6:
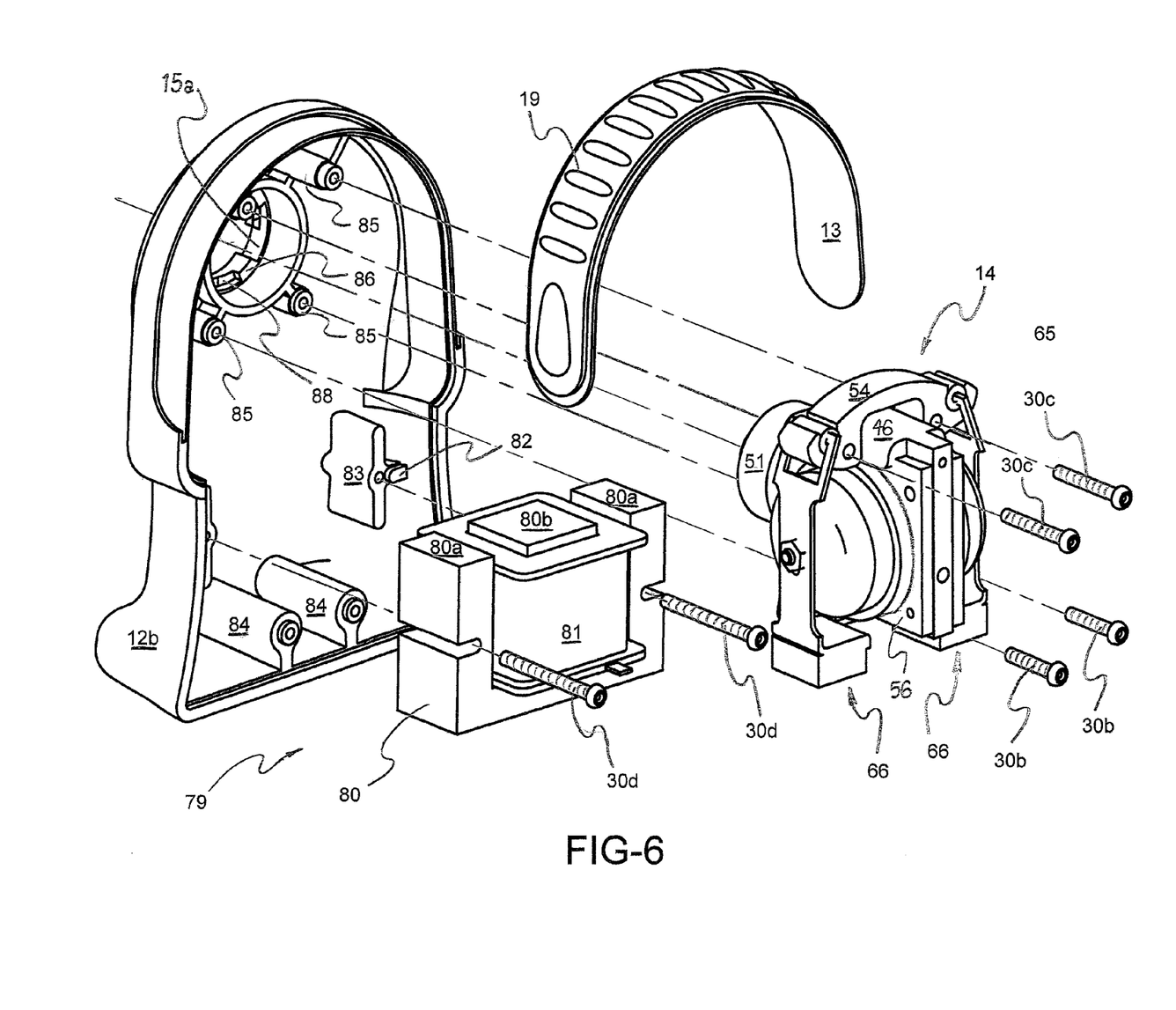

Referring to FIG. 6, a magnet core 80 may include outer legs 80a and a center leg 80b. A coil 81 wrapped around at least one of the legs 80b may provide alternating magnetic fields and thus alternating magnetic poles in the legs 80a, 80b. A tab 82 for registration of the magnet core 80 against the mount 83 provides alignment until the fasteners 30d can secure the magnet core 80 to the mounts 83.

Meanwhile, the mounts 84 may receive fasteners 30 to secure the rear portion 16a of the housing 12 to the front portion 16b of the housing 12. The mounts 85 may receive fasteners 30 securing the pump 14 thereto. For example, the fasteners 30b may penetrate apertures so designed to secure the pump 14 to the housing 12.

Also, the stops 86 may form part of the connector 15a in the housing 12 terminating any movement of the corresponding fastener 15b in the slots 88. The slots 88 receive tabs, portions of the connector 15b secured therein. The stops 86 provide registration and orientation of the atomizer 12 with respect to the housing 12. Passage of alternating current through the oil 81 alternates the polarity of the magnetism in the core leg 80a, 80b. Accordingly, each of the armature blocks 67 or armature magnets 67 is thus alternately pushed and pulled with respect to each of the legs 80a, 80b. Thus, the swing arms 66 oscillate about the yokes 65 secured to the retainer 54. The diaphragms 64 thus pump air through the valve bodies 56 and the pump body 46.

The flange 51 or nose 51 registers against the circumference of the connector 15 to position the pump 14 proximate the connector 15. Nevertheless, the actual outlet 11 of the pump 14 stands away from the connector 15a and near the center thereof. The atomizer 16 may connect directly to the outlet 11. Meanwhile, the connectors 15a, 15b cooperatively engage to properly register and stabilize the atomizer 16 with respect to the housing 12.

Figure 7:
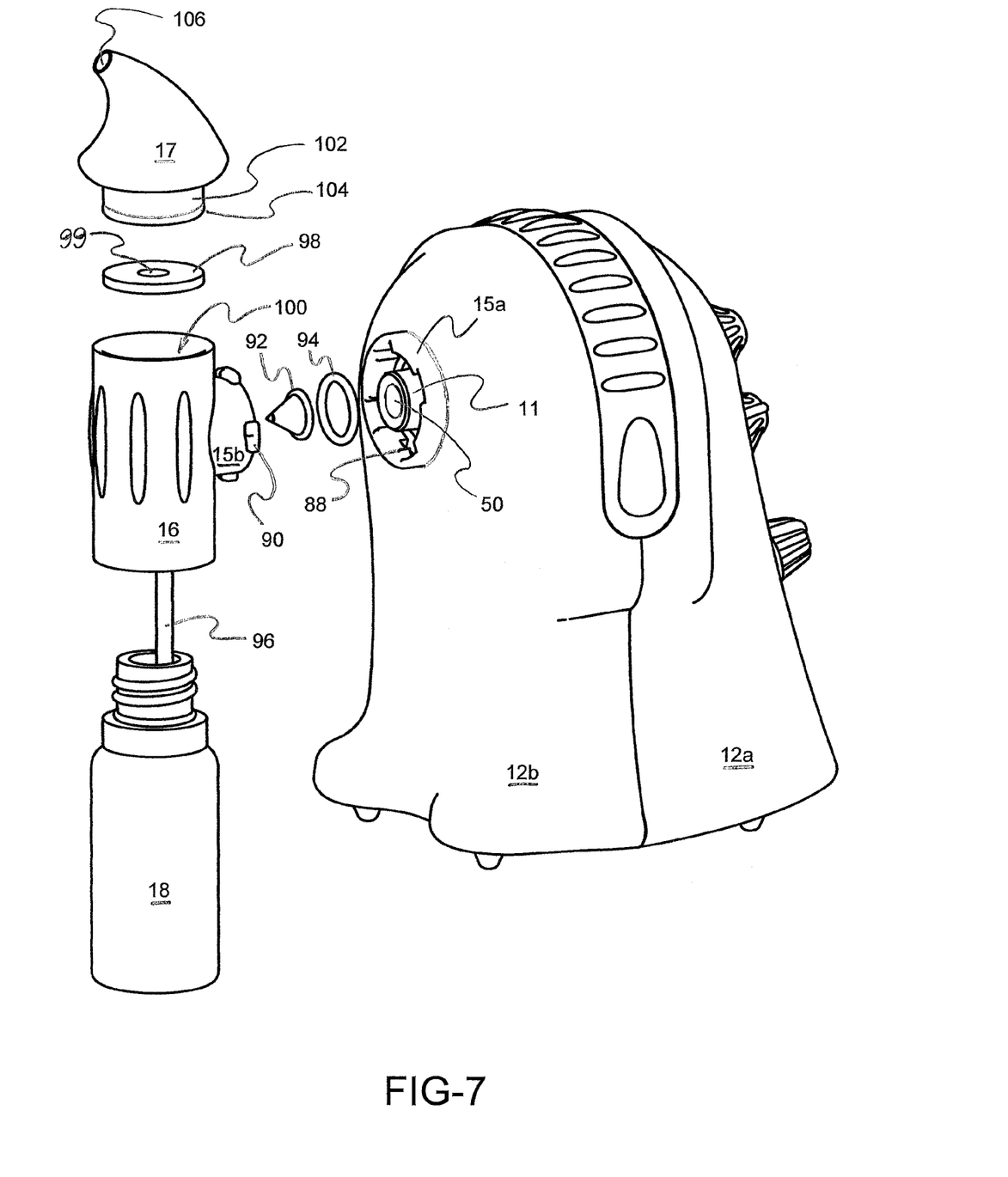
Figure 8:
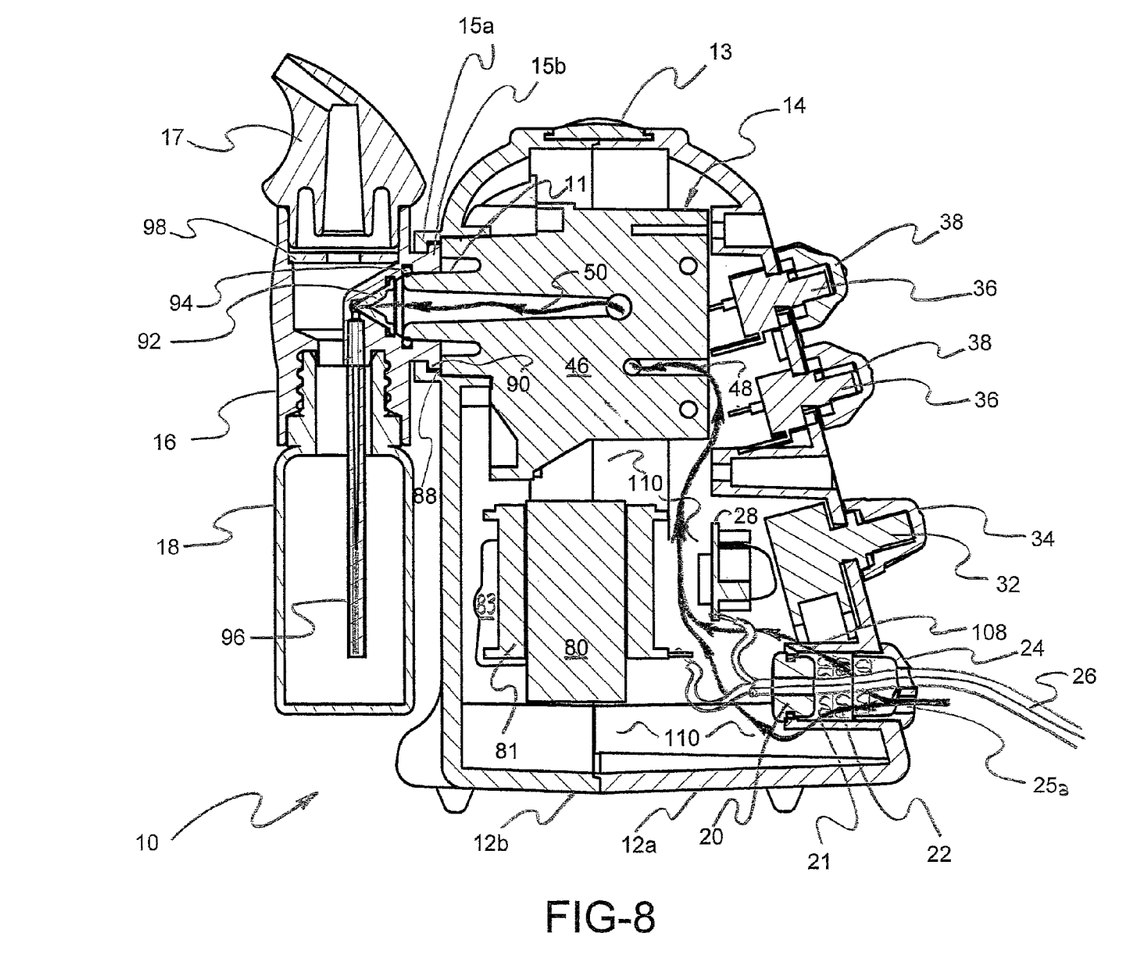
Figure 9:
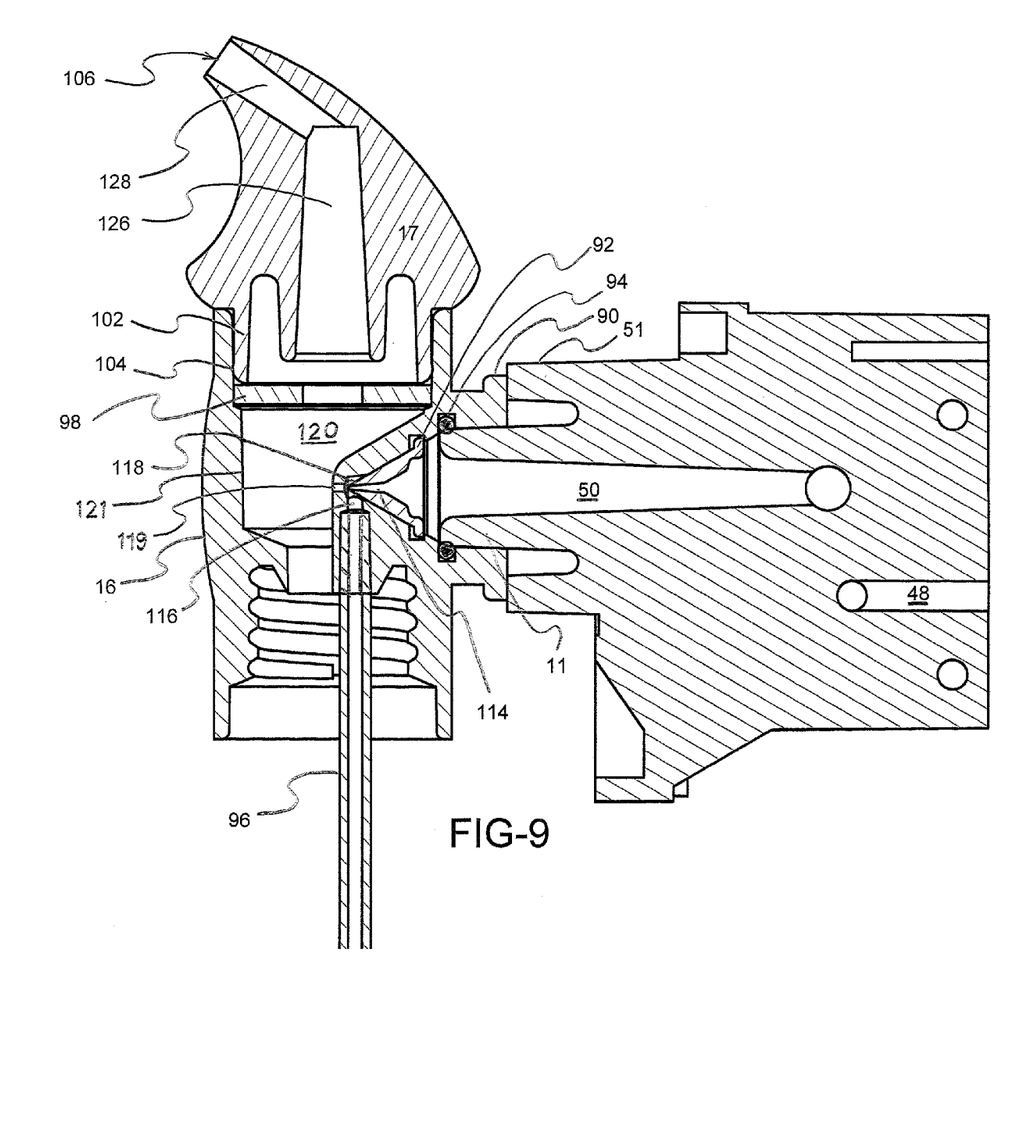

Referring to FIG. 7, tabs 90 formed as part of the connector 15b engage the slots 88 of the connector 15a. Rotation of the connector 15b aligns the tabs 90 with openings in the slots 88. Rotation after insertion provides locking of the tabs 90 in the slots 88, with a taper to secure the tabs 90 in certain embodiments.

A nozzle 92 may be formed separately from the main body 16 or atomizer 16. In the illustrated embodiment, the nozzle 92 fits into a cavity designed to have a vacuum drawn on it by virtue of expulsion from the nozzle 92 of air received from the pump 14. The nozzle 92 may be provided with various seals, or may be self sealing due to its configuration and the resilient nature of the materials from which it or the atomizer 16 are formed.

Meanwhile, the seal 94 provides sealing between the outlet 11 of the pump 14 and the atomizer 16. Direct engagement of the atomizer 16 with the outlet 11 is sealed against leakage of air by the seal 94. In the illustrated embodiment, the seal 94 is an 'O' ring. Eduction by the stream of air through the nozzle 92 draws a vacuum (e.g., reduced pressure) on the siphon 96, drawing liquid from the reservoir 18. The liquid from the reservoir 18 is partially atomized by the flow of air through the nozzle 92 as it educts as the liquid.

Eduction is a process of transferring momentum from a jet having mass and velocity into an adjacent material at a lower or zero velocity. The momentum of the jet of air passing out of the nozzle 92 creates a localized vacuum at the top of the siphon 96, drawing liquid up the siphon 96 from the reservoir 18, and transferring momentum into that liquid to atomize it and throw it into the atomizer 16. Upon impact with an opposite wall, the droplets further atomize into a cloud containing many more droplets of much smaller size than originally created by the nozzle 92.

A separator is formed by the main walls of the atomizer 16 and a separator plate 98. The separator plate 98 may include one or more apertures 99 located centrally, peripherally, or otherwise. Thus, impact of droplets educted by the nozzle 92 acting as an eductor 92 causes initial atomization. Impact against the walls of the atomizer 16 causes additional atomization as well as agglomeration of particles remaining adhered to the wall and otherwise dropping back toward the reservoir 18.

Likewise, the separator plate 98 passes the flow of air from the atomizer 16 through apertures 99 therein. Droplets that cannot move with the air flow, typically because they have too large a size and mass will not be able to quickly turn to follow the flow of air, and will strike the walls of the opening 100 or the separator plate 98. Thus, in a comparatively tiny space, including a length of less than about 1 inch of total travel, sometimes half an inch, the atomizer droplets are segregated.

Those that can be transported substantially indefinitely with the natural movement of ambient air drift away from the larger droplets. The larger droplets will quickly or comparatively quickly drift back down under the influence of gravity. Impact provides both agglomeration of droplets to each other, so they drip back into the reservoir 18. At the same time, more finely divided droplets form a cloud moving with the flow of air out of the opening 100 of the atomizer 16 and through the apertures 99 of the separator plate 98.

The distributor 17 may be provided with or otherwise formed to have a collar 102. The collar 103 may be sized to fit within the opening 100 of the atomizer 16. In one embodiment, a lip 104 may fit into a recess or relief formed within the wall of the atomizer 16, inside the opening 100. Thus, the collar 102 may be retained within the atomizer 16 by the lip 104 extending into or slightly into a relief, groove, slot, or the like.

A port 106 or exhaust 106 formed in the director 17 may serve to constrict, and thus increase the velocity of the flow passing from the director 17. The collar 102 may be formed to provide only modest resistence to rotation. Thus, the director 17 may be turned in a particular direction to discharge a jet of air containing the cloud of smallest atomized liquid droplets from the reservoir 18. The outlet 106 may smoothly transition the direction of flow from a vertical flow through the atomizer to a directed flow out the port 106.

In certain embodiments, the increase in area between the outlet on the nozzle 92 and the opening 100 causes a substantial increase in the cross-sectional area through which a stream of air travels. Accordingly, velocity will decrease and pressure will increase. By the same token, passing through the director 17 and out the port 106, the air flow will once again be constricted to less cross-sectional area and thus increase in velocity by decreasing in pressure or static pressure as it exits. A benefit of the director 17, and particularly the geometry thereof along with the size of the aperture 106 or port 106 is to direct a jet that can further assist in distribution, direction, and evaporation of the oils or other materials comprised in the liquid within the reservoir 18.

Evaporation is a function of vapor pressure of a material, local concentration, and surface area available to evaporate molecules therefrom. Thus, the smaller the effective diameter of various droplets of liquid, the higher the rate of evaporation of the liquid. Notwithstanding oils may be highly volatile or may be barely volatile, all have a vapor pressure. Even mercury has a vapor pressure, a very low one. Thus, an atomizer 16 in accordance with the invention may greatly increase evaporation rate by the subdivision of liquid into droplets having more surface area. Typical diameters are on the order of 1 to 5 microns. The various components are sized to cause air flows that will twist and turn sufficiently to recapture and return most the droplets above these sizes back into the reservoir.

Referring to FIG. 8, a quasi schematic, cross-sectional, side elevation view of the apparatus 10 illustrates the flow of air through the housing 12, pump 14, and the atomizer 16. Air is drawn initially through the ports 25 or apertures 25 in the cap 24. Air flows from the environment through the ports 25 and filters 22 or filter media 22 placed within the recess 21. The recess 21 also serves to hold the grommet 20 relieving stress on the power cord 26.

Once inside the cavity 110 of the housing 12, air finds its way to the passage 48 in the pump body 46. Once in the passage 48, air flows through the pump body 46, and is divided between the two sides of the pump 14, passing into the respective compression chambers 53 of each of the valve bodies 56.

Upon compression of air within the valve bodies 56 by the diaphragms 64, reed valves 60 conduct the higher pressure air into the passage 50. Initially, the air passes perpendicularly to the face 78 of the pump body 46, but then turns within the passage 50 traveling parallel to the face 78 to exit out of the outlet 11.

Notwithstanding the atomizer 16 is secured by the connector 15*b* to the connector 15*a* of the housing 12, the actual fluid connection between the atomizer 16 and the pump 15 is direct. That is, for example, the seal 94 between the atomizer 16 and the outlet 11 of the pump 14 provides the actual air seal between the atomizer 16 of the pump 14. Meanwhile, the shape of the nozzle 92 and its cooperative, fitted groove in the atomizer 16 provides a seal therebetween. Thus, the interior of the nozzle 92 is completely sealed by the seal 94, the outlet 11, and the body of the atomizer 16, in addition to the surfaces of the nozzle 92, itself.

The nozzle receives air from the passage 50, and passes it into the atomizer 16. This is best shown by reference to FIG. 9. Referring to FIGS. 8-9, while continuing to refer generally to FIGS. 1-7 as well, the nozzle 92 encloses a cavity 114 or channel 114 leading from the passage 50 toward an orifice 118.

The orifice 118 is located within a cavity 116 sealed by the shape of the nozzle 92 itself. The cavity 116 has three openings. From the pump side, the cavity is open to the orifice 118 of the nozzle 92. From below, the cavity 116 is open to the siphon 96 leading to the reservoir 18. Toward the atomizer 16, the cavity 116 is open to yet another orifice 119. The exit orifice 119 permits discharge of fluids including air from the orifice 118 and liquid from the siphon tube 96 out the exit orifice 119.

The nozzle 92, and particularly the orifice 118, acts as an eductor transferring momentum to the surrounding air, and tending to evacuate the chamber 119. Thus, the reduced pressure in the chamber 116 draws liquid through the siphon tube 96 from the reservoir 18. Liquid is not only drawn in, but also comminuted by the blast of high speed air, comparatively speaking, from the orifice 118.

The liquid from the siphon 96 is atomized into droplets of various sizes. The entire mixture of air and droplets passes through the exit orifice 119 toward the separator 120, and particularly toward the wall 121 thereof. Having received momentum from the jet of air passing out of the orifice 118, the entrained droplets in the air jet obtain another momentum transfer as they dash against the wall 121. Large droplets break into smaller droplets. Some droplets agglomerate against the wall 121 and begin to drift or drip down toward the reservoir 18. Other droplets, having comparatively smaller effective diameters, are more easily entrained in the air, and pass with it through the separator chamber and out apertures 122 in the separator plate 98.

The separator plate may have one or more apertures 122 located about the periphery thereof, distributed throughout, or axially centered. In certain embodiments, apertures 122 may feed air into the traps 124 of the director 17. Again, droplets that are too large to stay with the flow of air will be trapped in the traps 124, and eventually return back to the separator plate 98 to eventually be re-entrained or find their way to the reservoir 18.

The net flow of air passes through the aperture 122 of the separator plate 98, on its way into the passages 126 and 128 of the director 17. Ultimately, the jet of air expelled from the port 106 carries with it only those droplets that are sufficiently small, typically on the order of from about 1 to about 5 microns in diameter such that they will drift substantially indefinitely with ambient air movement as they evaporate.

The controller 32, such as a rheostat 32, or the like, provides a control over the voltage, thus the energy provided by the magnets 80 driving the pump 14. Meanwhile, the controllers 34, 36, such as potentiometers, for example, provide control over the delay time and the operational time of the magnets 80. Thus, a completely arbitrary ratio of duty cycle as a function of total time or as a portion of total time may be selected.

In certain embodiments, the duty cycle options may be limited between finite limits in order to prevent actual zero points. Nevertheless, by the mathematically independently variable controls between maximum and minimum extreme, each of the controls 32, 34, 36 may provide arbitrarily selectable values for volume of air, delay time, and operation time, respectively.

By having an extra mathematical variable available, the apparatus 10 provides to a user control of an additional output. Typically, a user may control the duty cycle in order to provide maximum efficiency of atomization of the apparatus 10, with minimum use of energy, and with minimum use of essential oils or other aromatic materials maintained in the reservoir 18. In certain embodiments, delay time may range from about one hundredth of a minute to about one hour. In alternative embodiments, delay times may range from about several seconds to about half an hour. In one presently contemplated embodiment, minimum limits for both the delay and the operation times may be set at a one minute minimum with a 20 to 30 minute maximum. These operational limits have been found to be very practical and can meet the needs of most users.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of aroma therapy comprising;
    providing an atomizer comprising an eductor and a separator, the atomizer being connected directly to a reservoir and to a pump anchoring the atomizer to a supporting surface;
    the providing an atomizer wherein the eductor comprises a nozzle having a minimum effective diameter discharging the flow therethrough and into an aperture spaced therefrom a distance of from about one to about 10 times the minimum effective diameter;
    adjusting an electronic controller to control at least one of a duration of operation and a duration of a delay between periods of operation of the pump;
    operating the pump to pressurize ambient air into a flow through the atomizer;
    educting a liquid directly from the reservoir into the flow;
    atomizing the liquid into droplets by the educting and by colliding against a wall of the separator;
    separating the droplets by size;
    recovering comparatively larger droplets into the reservoir;
    passing comparatively smaller droplets from the atomizer out through the separator with the flow; and
    simultaneously limiting net outflow of the liquid and decreasing mean droplet size by selectively controlling by a user the duty cycle of the pump.

2. The method of claim 1, further comprising controlling the duty cycle by controlling the ratio of the duration of operation to the duration of the delay plus the duration of operation.

3. The method of claim 2, further comprising connecting a first connector of the atomizer directly to the pump, a second connector thereof directly to the reservoir, and a third connector thereof directly to a distributor.

4. The method of claim 3, wherein the atomizer is homogeneously molded with the first, second, and third connectors.

5. A method of aroma therapy comprising;
    providing an atomizer, homogeneously molded and comprising an eductor, separator, pump, and first, second, and third connectors;
    the providing the atomizer, wherein the atomizer is connected by the first connector directly to the pump, by the second connector directly to the reservoir, and by the third connector directly to a distributor, the pump anchoring the atomizer to a supporting surface;
    adjusting an electronic controller to control the duty cycle by at least one a duration of operation, a duration of a delay between periods of operation of the pump, and a ratio corresponding thereto;
    operating the pump to pressurize ambient air into a flow through the atomizer;
    educting a liquid directly from the reservoir into the flow;
    atomizing the liquid into droplets by the educting and by colliding against a wall of the separator;
    separating the droplets by size;
    recovering comparatively larger droplets into the reservoir;
    passing comparatively smaller droplets from the atomizer out through the separator with the flow;
    simultaneously limiting net outflow of the liquid and decreasing mean droplet size by selectively controlling by a user the duty cycle of the pump; and
    providing a housing, a motor inside the housing and electrically powered to drive the pump, the housing further comprising a lock securing the atomizer to the pump.

6. The method of claim 5, wherein the pump is located in a housing having a filter disposed in an aperture thereof receiving a cord providing power to the motor, the aperture serving to support stress on the cord and pass the flow from the environment to the pump.

7. A method of aroma therapy comprising:
    providing an atomizer comprising an eductor and a separator, the atomizer being connected directly to a reservoir and to a pump anchoring the atomizer to a supporting surface;
    adjusting an electronic controller to control at least one of a duration of operation and a duration of a delay between periods of operation of the pump;
    operating the pump to pressurize ambient air into a flow through the atomizer;
    educting a liquid directly from the reservoir into the flow;
    atomizing the liquid into droplets by the educting and by colliding against a wall of the separator;
    separating the droplets by size;
    recovering comparatively larger droplets into the reservoir;
    passing comparatively smaller droplets from the atomizer out through the separator with the flow; and
    simultaneously limiting net outflow of the liquid and decreasing mean droplet size by selectively controlling by a user the duty cycle of the pump;

the atomizer, wherein the pump comprises a pump body fitted with a valve plate captured in a pinch slot to support pressure between the pump body and valve plate.

8. The method of claim 7, wherein the pump further comprises seals positioned about openings passing the flow into and out of the pump, the seals minimizing pressure exposure of the structure of the pump by being sized to fit within about two diameters of apertures corresponding thereto.

9. A method of atomizing, the method comprising:
providing a pump disposed within a housing, driven by a motor, and comprising a diaphragm compressing air and providing a flow thereof at a pressure greater than ambient pressure, the motor comprising a coil and a first magnet operably connected to reciprocate the first magnet back and forth to drive the diaphragm;
providing a separator plate controlling outflow, separating the comparatively larger droplets from the comparatively smaller droplets prior to exit of the comparatively smaller droplets from the atomization;
providing an eductor comprising a nozzle having a minimum effective diameter discharging the flow therethrough and into an aperture spaced therefrom a distance of from about one to about 10 times the minimum effective diameter;
providing a control system infinitely variable between extremes by a user to arbitrarily select at least one of a duration of operation and a duration of deactivation between periods of operation of the motor;
providing a bottle containing a liquid comprising a scent;
connecting an atomizer directly to the bottle,
securing the atomizer directly to the pump anchoring the atomizer to a supporting surface;
drawing from the bottle a portion of the liquid by eduction;
atomizing the portion into droplets;
spraying the droplets into a separator removing droplets insufficiently small to be carried indefinitely by ambient air movement.

10. The method of claim 9, wherein the separator and flow are sized to release droplets having an effective diameter of from about 1 micron to about 5 microns.

11. The method of claim 10, further comprising connecting the pump directly to the atomizer, operating the pump providing the flow, increasing the velocity of the flow by constricting the flow through a nozzle, and educting the liquid from the bottle into the flow as droplets.

12. The apparatus of claim 11, wherein the atomizer further comprises a body having the first fitting, second fitting, and third fittings homogeneously molded therewith, the first fitting directly receiving and securing the bottle, the second fitting containing the eductor, and a third fitting containing a distributor releasing the flow into the ambient.

13. The method of claim apparatus of claim 12, further comprising conducting aroma therapy comprising:
selecting the liquid to be an essential oil containing substantially no diluents;
selecting by a user a first time period corresponding to operation of the pump, arbitrarily selected between a first minimum time and a first maximum time;
selecting by a user a second time period corresponding to a delay in operation of the pump, the delay arbitrarily selected between a second minimum time and a second maximum time.

14. An apparatus comprising:
a housing;
a pump disposed within the housing and comprising a diaphragm compressing air to a pressure greater than ambient pressure;
a motor comprising a coil and a first magnet
the motor, wherein the coil is operably connected to reciprocate an electric field to activate the first magnet;
the motor, wherein the first magnet drives a second magnet back and forth to oscillate the diaphragm;
a control system operably connected to the coil to control electricity flowing to the coil;
an atomizer, integrated with the pump, the atomizer being anchored by the pump and receiving directly therefrom a flow of pressurized air;
the atomizer further comprising a first fitting directly receiving and securing a bottle containing an aromatic scent thereto, a second fitting containing an eductor, and a third fitting containing a distributor releasing the pressurized air into the ambient;
a separating chamber and a separator plate controlling outflow from the separator chamber, separating comparatively larger droplets from comparatively smaller droplets prior to exit of the comparatively smaller droplets from the atomizer; and
an eductor comprising a nozzle having a minimum effective diameter discharging the flow therethrough and into an aperture spaced therefrom a distance of from about one to about 10 times the minimum effective diameter.

15. The apparatus of claim 14, wherein the control system further comprises an actuator adjustable by a user to selectively and arbitrarily control the duration of delivery of electrical energy to the coil.

16. The apparatus of claim 14, wherein the control system further comprises an actuator adjustable by a user to selectively and arbitrarily control a delay between adjacent periods of continuous delivery of electrical energy to the coil.

17. The apparatus of claim 14, wherein the control system further comprises:
an actuator, adjustable and infinitely variable by a user between extremes, selectively and arbitrarily controlling the duration of delivery of electrical energy to the coil and a delay between adjacent periods of continuous delivery of electrical energy to the coil.

18. The apparatus of claim 14, wherein the atomizer further comprises a body having the first fitting, second fitting, and third fittings homogeneously molded therewith.

* * * * *